United States Patent [19]

Sakamoto et al.

[11] 4,428,806

[45] Jan. 31, 1984

[54] PROCESS FOR PRODUCING BROMINATED 1,3-DIOXOLEN-2-ONES

[75] Inventors: Fumio Sakamoto, Osaka; Shoji Ikeda, Ibaraki; Goro Tsukamoto, Toyanaka; Isamu Utsumi, Kyoto, all of Japan

[73] Assignee: Kanebo Ltd., Tokyo, Japan

[21] Appl. No.: 426,158

[22] Filed: Sep. 28, 1982

[30] Foreign Application Priority Data

Oct. 30, 1981 [JP] Japan ................................. 56-172719

[51] Int. Cl.$^3$ ............................................ B01J 19/12
[52] U.S. Cl. ............................ 204/158 HA; 549/229
[58] Field of Search ................. 204/158 HA; 549/229

[56] References Cited

U.S. PATENT DOCUMENTS 3,020,290  2/1962  Moss ............................ 204/158 HA
3,152,146 10/1964  Baker et al. ........................ 549/229

OTHER PUBLICATIONS

Liebigs Ann. Chem., 1977, pp. 27–32.

*Primary Examiner*—Howard S. Williams

[57] ABSTRACT

A process for producing a brominated 1,3-dioxolen-2-one of the following general formula (I)

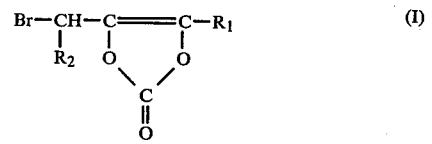

wherein $R_1$ represents a hydrogen atom, a methyl group, or an aryl group, and $R_2$ represents a hydrogen atom, or $R_1$ and $R_2$ may be bonded together to form $-(CH_2)_n-$ in which n represents an integer of 3 to 5, which comprises reacting a compound of the following formula (II)

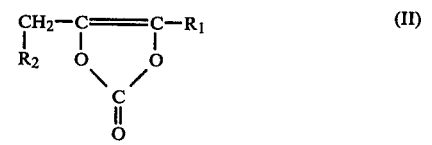

wherein $R_1$ and $R_2$ are as defined, with bromine under radical generating conditions.

9 Claims, No Drawings

PROCESS FOR PRODUCING BROMINATED 1,3-DIOXOLEN-2-ONES

This invention relates to a process for producing novel derivatives of 1,3-dioxolenes, and more specifically, to an advantageous process for producing novel brominated 1,3-dioxolen-2-ones useful as modifiers for prodrug preparation in medicines.

Some medicines, despite their high pharmacological activities, cannot fully exhibit their utility as medicines because of chemical instability or poor bioavailability, and as one method for remedying this defect, such medicines are chemically modified to form prodrugs. For example, a drug having a low intestinal absorption may be chemically modified to increase its intestinal absorption and the modified drug may be converted back to the original drug in vivo by a chemical and biological action, thus exhibiting the inherent pharmacological activity of the drug.

For this purpose, various modifying groups have been proposed up to date but have not proved to be entirely satisfactory in respect of the chemical stability of the resulting prodrugs, their convertibility to the original drugs in vivo, side-effects caused by the modifying groups, etc.

It is an object of this invention to provide an advantageous process for producing brominated 1,3-dioxolen-2-ones of general formula (I) which are useful as modifiers for prodrug preparation in medicines.

The products of the invention represented by general formula (I)

$$\text{Br—CH—C}{=\!=\!=}\text{C—R}_1 \atop {|\quad\;|\quad\;|\atop R_2\;\;O\quad O}\;\;\diagdown\!\!\underset{\underset{O}{\|}}{C}\!\!\diagup \qquad (I)$$

wherein $R_1$ represents a hydrogen atom, a methyl group or an aryl group such as a phenyl group, and $R_2$ represents a hydrogen atom, or $R_1$ and $R_2$ may be bonded together to form —$(CH_2)_n$— in which n is an integer of 3 to 5, are novel compounds not disclosed in the literature. Specific examples include
4-bromomethyl-1,3-dioxolen-2-one,
4-bromomethyl-5-methyl-1,3-dioxolen-2-one,
4-bromomethyl-5-phenyl-1,3-dioxolen-2-one,
3-bromo-1,2-carbonyldioxycyclohexene, and
3-bromo-1,2-carbonyldioxycyclooctene.

All these brominated 1,3-dioxolen-2-ones easily react with carboxylic acids, thiocarboxylic acids, or phenols to give the corresponding esters or ethers. These esters and ethers are stable in neutral and acidic media, and are relatively stable in an alkaline medium simulating the intestinal juice in spite of the fact that they readily undergo hydrolysis under alkaline hydrolysis conditions in ordinary chemical reactions. In addition, they are easily hydrolyzed in the presence of an enzyme in vivo and thus converted back to their original compounds.

For example, when a penicillin having a carboxyl group is reacted with the brominated 1,3-dioxolen-2-one of general formula (I), the corresponding ester is formed. This ester is stable in the gastric and intestinal juices, and is easily absorbed from the intestinal trace. At the same time, it is easily hydrolyzed in vivo to the original penicillin. Thus, the brominated 1,3-dioxolen-2-ones of general formula (1) are useful especially as modifiers for prodrug preparation in medicines. Esters and ethers derived from carboxylic acids and phenols and the brominated 1,3-dioxolen-2-ones of this invention are stable in neutral and acidic media as mentioned above but readily undergo hydrolysis under ordinary alkaline hydrolysis conditions. Hence, the brominated 1,3-dioxolen-2-ones of this invention are also useful as reagents for introduction of protective groups in chemical reactions.

The utility of the product of formula (I) of this invention will be described below by citing experimental data in regard to prodrugs of ampicillin.

Blood level in oral administration

1. Test compounds
   A: Ampicillin (5-methyl-2-oxo-1,3-dioxolen-4-yl) methyl ester hydrochloride (synthesized in accordance with Referential Example 3 given below from ampicillin trihydrate and 4-bromomethyl-5-methyl-1,3-dioxolen-2-one)
   B: Ampicillin phthalidyl ester hydrochloride (known ampicillin ester, a control compound)
   C: Ampicillin trihydrate (a control compound)
2. Testing method Each of the test compounds (as an aqueous solution having a concentration of 5 mg/ml as ampicillin) was orally administered in a dose of 50 mg/kg as ampicillin to four week old mice (ddY-strain, body weight about 20 g, five per group) which were caused to fast overnight. The blood was taken from the mice periodically, and the concentration of ampicillin in the serum was measured by a bioassay method. The blood Ampicillin level ratio was calculated from the following equation.

$$\text{Ampicillin level ratio} = \frac{\text{Serum Ampicillin level in administration of each of the compounds A, B and C}}{\text{Serum Ampicillin level in administration of the compound C}}$$

3. Results

TABLE 1

| | Item | | | | | |
|---|---|---|---|---|---|---|
| | Ratio of the concentration of ampicillin in the serum Blood letting time (min.) | | | | | |
| Test compound | 15 | 30 | 60 | 90 | 120 | 180 |
| A | 2.8 | 2.9 | 2.1 | 1.8 | 1.5 | 1.3 |
| B | 3.0 | 1.8 | 1.4 | 1.1 | 0.9 | 0.8 |
| C | 1.0 | 1.0 | 1.0 | 1.0 | 1.0 | 1.0 |

It is seen from Table 1 that the ampicillin ester (A) derived from the compound of this invention is easily absorbed and converted back to the original ampicillin in vivo, and shows a high blood level over a longer period of time than ampicillin (C) and the known ampicillin ester (B).

Hydrolysis in an acidic medium (simulating the gastric juice)

1. Test compounds: A and B above
2. Testing method

Each of the test compounds was dissolved in an acidic medium (pH 1.2) consisting of 2.0 g of sodium chloride, 24 ml of 10% hydrochloric acid, 3.2 g of pepsin and 1000 ml of water. The solution was shaken at 37° C., and sampled periodically. The sample was subjected to high-performance liquid chromatography using a reversed phase partition column, and the degree of hydrolysis of each of the test compounds was determined from a decrease in its peak height.

3. Results

TABLE 2

| Test compound | Item | | | | |
|---|---|---|---|---|---|
| | Degree of hydrolysis in an acidic medium (%) | | | | |
| | Sampling time (hours) | | | | |
| | 1 | 2 | 4 | 6 | 20 |
| A | 7 | 15 | 20 | 28 | 52 |
| B | 18 | 31 | 43 | 55 | 100 |

The results given in Table 2 demonstrate that the ampicillin ester (A) derived from the compound of this invention is much more stable than the known control compound (B).

Hydrolysis in a basic medium (simulating the intestinal juice)

1. Test compounds: A and B above
2. Testing method

Each of the test compounds was dissolved in a basic medium (pH 7.5) consisting of 35.8 g of disodium phosphate, 6.0 ml of 10% hydrochloric acid and 2.8 g of pancreatin and 1000 ml of water, and the degree of hydrolysis of each test compound was determined as in the case of the acidic medium.

3. Results

TABLE 3

| Test compound | Item | | | | |
|---|---|---|---|---|---|
| | Degree of hydrolysis in a basic medium (%) | | | | |
| | Sampling time (min.) | | | | |
| | 5 | 10 | 20 | 30 | 60 |
| A | 16 | 32 | 48 | 65 | 80 |
| B | 39 | 61 | 90 | 95 | 100 |

The results given in Table 3 demonstrate that in the basic medium, the ampicillin ester (A) derived from the compound of this invention is much more stable than the known control compound (B).

Toxicity

The toxicity ($LD_{50}$) of the compound A was examined by using four week old ddY-strain mice, and the results were as follows:

Oral administration: >5,000 mg/kg
Intraperitoneal administration: 1430 mg/kg
Intravenous administration: 557 mg/kg.

The present invention provides an industrially advantageous process for producing the brominated 1,3-dioxolen-2-ones of formula (I) having utility as described above.

This process is performed by reacting a 1,3-dioxolen-2-one of general formula (II)

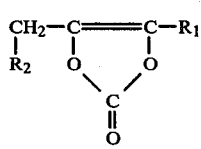

(II)

wherein $R_1$ and $R_2$ are as defined above, with bromine ($Br_2$).

Many reagents and operating methods have been known heretofore with regard to the bromination of organic compounds. The simplest method involves the use of bromine which is an economically advantageous reagent because of its availability and low cost.

However, when molecular bromine ($Br_2$) is used in the bromination of a methylene group (to be referred to as the allylic position) adjacent to a double bond, an addition reaction of bromine to the double bond proceeds predominantly even under radical reaction conditions. Hence, a large amount of a by-product is formed, and it is impossible to obtain the desired compound brominated at the allylic position in good yields. For this reason, N-bromo compounds, such as N-bromosuccinimide, are usually employed for the bromination of the allylic position (see Methoden der Organischen Chemie (Houben-Weyl), Vol. v/4, pages 38-39 and 219-220, 1960).

The present inventors have extensively investigated a process for producing the compounds of general formula (I) industrially advantageously, and unexpectedly found that bromine can be suitably applied to the allylic bromination of the compounds of general formula (II) to give the desired products in high yields.

The present invention will now be described in greater detail.

According to this invention, the compound of general formula (I)

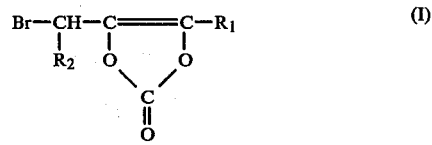

(I)

wherein $R_1$ and $R_2$ are as defined above, can be produced advantageously by reacting a compound of general formula (II)

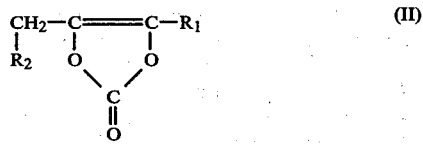

(II)

wherein $R_1$ and $R_2$ are as defined above, with bromine under radical generating conditions.

The starting compounds of general formula (II) can be synthesized by the known method disclosed in Liebigs Annalen der Chemie, Vol. 764, pages 116-124 (1972), Tetrahedron Letters, 1972 pages 1701-1704, and U.S. Pat. No. 3,020,290.

The process of this invention is carried out preferably in an aprotic inert organic solvent, for example halogenated aliphatic saturated hydrocarbons such as carbon tetrachloride and tetrachloroethane and aromatic hydrocarbons such as benzene and chlorobenzene.

The amount of bromine used is about 1.0 to about 1.5 moles, preferably about 1.05 to about 1.2 moles, per mole of the starting compound of formula (II). If the amount of bromine is below the above-specified lower limit, the starting compound (II) remains unreacted, and if the amount of bromine exceeds the specified upper limit, there is a greater tendency toward the formation of large amounts of by-products. For example, in the case of 4,5-dimethyl-1,3-dioxolen-2-one (a compound of formula (II) in which $R_1$ is methyl and $R_2$ is hydrogen), the proportion of a bisbromomethyl compound of the following formula increases.

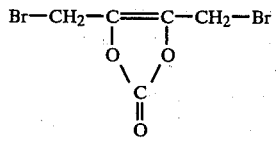

Hence, amounts outside the specified range are undesirable.

The radical generating conditions in accordance with this invention include, for example, ultraviolet radiation. Low-pressure and high-pressure mercury lamps may be utilized as a source of ultraviolet radiation. When ultraviolet radiation is employed, the reaction proceeds even at room temperature (about 20° C.), and no particular heating is necessary. If desired, however, the reaction may be carried out at the boiling point of the solvent. The preferred reaction temperature is from about 20° C. to about 80° C.

The radical-generating conditions in accordance with this invention also include the use of a known radical initiator such as benzoyl peroxide, lauroyl peroxide, α,α'-azobisisobutyronitrile, and αα'-azobis-2,4-dimethylvaleronitrile. The amount of the radical initiator may be a catalytic one. Usually, it is 0.1 to 5% by weight based on the starting compound of formula (II). When the radical initiator is used, the reaction temperature is preferably about 40° C. to about 100° C., more preferably about 50° C. to about 80° C.

The reaction is carried out preferably in an inert atmosphere, for example in an atmosphere of nitrogen or argon.

The process of this invention is performed under the aforesaid conditions. As a specific operational procedure, it is preferred, for example, to dissolve the starting compound (II) in an organic solvent, and add a predetermined amount of bromine dropwise while the solution is well stirred under the radical generating conditions. Preferably, bromine is used as a solution in the aforesaid reaction solvent. Upon the dropwise addition of bromine, the reaction mixture assumes a color peculiar to bromine. Since the bromine color disappears as the reaction proceeds, it is advisable to supply additional drops of bromine substantially as the disappearance of the bromine color occurs. The reaction time varies according to the radical generating conditions, the temperatures, etc. For example, it is 10 minutes to 5 hours. Usually, the reaction ends within 2 hours.

According to the above process, the desired compound of formula (I) is obtained in a yield of as high as about 70% under preferred conditions.

Investigations of the present inventors have shown that the yield of the desired compound (I) can be further increased by employing additional means described below. According to the aforesaid basic process, the desired compound of formula (I) can be obtained in a high yield amounting to 70%. But a side-reaction of forming a by-product having bromine added to the double bond is formed, and it is difficult to increase the yield of the compound (I) further.

The present inventors have succeeded in increasing the yield of the compound (I) by about 10% by carrying out the aforesaid basic process in the presence of a basic inorganic compound in the reaction system. Examples of suitable basic inorganic compounds for use in this invention include alkali bicarbonates such as sodium bicarbonate and potassium bicarbonate, alkali carbonates such as sodium carbonate and potassium carbonate.

The basic inorganic compound is used, for example, in an amount of 0.1 to 1.0 mole per mole of bromine. It is suspended in the reaction mixture and stirred well.

As stated in detail hereinabove, the present invention gives the useful compounds of general formula (I) in high yields by the method involving the use of bromine which has previously been considered as difficult to apply to the production of allylic brominated products in high yields. Bromine as a starting material is available at low cost, and the reaction operation is simple.

The following Examples and Referential Examples illustrate the present invention specifically.

EXAMPLE 1

Production of 4-bromomethyl-5-methyl-1,3-dioxolen-2-one 5.7 g of 4,5-dimethyl-1,3-dioxolen-2-one (synthesized in accordance with Tetrahedron Letters, 1972, pages 1701–1704) was dissolved in 200 ml of benzene, and under a nitrogen gas atmosphere, 8.8 g of bromine in 40 ml of benzene was added dropwise with stirring over the course of 90 minutes while irradiating ultraviolet light from a mercury lamp (model EL-A-10, a product manufactured by Eiko Sha) at room temperature. Subsequently, the mixture was stirred for 30 minutes. The reaction mixture was concentrated, and the resulting syrup was distilled under reduced pressure to give 6.6 g (yield 68.4%) of the desired product as a colorless liquid having a boiling point of 115° to 120° C./5 mmHg. The product was again distilled, the resulting pure poduct having a boiling point of 95° to 100° C./2 mmHg was used in the following analyses.

| Elemental analysis for $C_5H_5O_3Br$: | | | |
|---|---|---|---|
| | C | H | Br |
| Calculated (%): | 31.12 | 2.61 | 41.40 |
| Found (%): | 31.35 | 2.30 | 41.32 |

IR (neat, $\nu cm^-$): near 1825 (carbonyl).
NMR ($CCl_4$, δppm): 2.10 (3H, —$CH_3$, s), 4.10 (2H, —$CH_2Br$, s).

EXAMPLE 2

Production of 4-bromomethyl-5-methyl-1,3-dioxolen-2-one 5.7 g of 4,5-dimethyl-1,3-dioxolen-2-one was dissolved in 200 ml of benzene, and 4.7 g of sodium hydrogen carbonate was added. Under a nitrogen gas atmosphere, 8.8 g of bromine in 40 ml of benzene was added dropwise over the course of 90 minutes with stirring while ultraviolet light was irradiated at room temperature from a mercury lamp (Model EL-A-10, manufactured by Eiko Sha). Subsequently, the mixture was stirred for 30 minutes. The insoluble materials were separated by filtration, and the filtrate was concentrated. The resulting syrup was distilled under reduced pressure to give 7.6 g (yield 78.8%) of the desired product as a colorless liquid having a boiling point of 115° to 120° C./5 mmHg. The IR and NMR spectral data of this product agreed with those of the product obtained in Example 1.

EXAMPLE 3

Production of 4-bromomethyl-5-methyl-1,3-dioxolen-2-one 5.7 g of 4,5-dimethyl-1,3-dioxolen-2-one was dissolved in 200 ml of carbon tetrachloride. Under a nitrogen gas atmosphere, 40 mg of α,α'-azobisisobutyronitrile was added at 70° C. With vigorous stirring, 8.8 g of bromine in 40 ml of carbon tetrachloride was added dropwise over the course of 50 minutes. Subsequently, the mixture was stirred for 15 minutes at the same temperature. The reaction mixture was concentrated, and the resulting syrup was distilled under reduced pressure to give 6.5 g (yield 67.4%) of the desired product as a colorless liquid having a boiling point of 115° to 120° C./5 mmHg. The IR and NMR spectral data of this product agreed with those of the product obtained in Example 1.

EXAMPLE 4

Production of 4-bromomethyl-5-methyl-1,3-dioxolen-2-one 5.7 g of 4,5-dimethyl-1,3-dioxolen-2-one was dissolved in 200 ml of carbon tetrachloride, and 4.7 g of sodium hydrogen carbonate and 40 mg of α,α'-azobisisobutyronitrile were added. Under a nitrogen gas atmosphere, 8.8 g of bromine in 40 ml of carbon tetrachloride was added dropwise over the course of 50 minutes with vigorous stirring at 70° C. Subsequently, the mixture was stirred for 15 minutes at the same temperature. After cooling the insoluble materials were separated by filtration, and the filtrate was concentrated. The resulting syrup was distilled under reduced pressure to give 7.8 g (yield 80.8%) of the desired product as a colorless liquid having a boiling point of 115° to 120° C./5 mmHg. The IR and NMR spectral data of this product agreed with those of the product obtained in Example 1.

EXAMPLE 5

Production of 4-bromomethyl-5-phenyl-1,3-dioxolen-2-one 8.8 g of 4-methyl-5-phenyl-1,3-dioxolen-2-one (synthesized in accordance with Liebigs Annalen der Chemie, Vol. 764, pages 116–124, 1972) was dissolved in 200 ml of benzene, and 4.7 g of sodium hydrogen carbonate and 40 mg of benzoyl peroxide were added. Under a nitrogen gas atmosphere, 8.8 g of bromine in 40 ml of benzene was added dropwise over the course of 50 minutes with vigorous stirring at 70° C. Subsequently, the mixture was stirred for 15 minutes at the same temperature. After cooling, the insoluble materials were separated by filtration, and the filtrate was concentrated. The residue was recrystallized from a mixture of benzene and cyclohexane to give 10.1 g (yield 79.2%) of the desired product as colorless needles having a melting point of 90.5° to 91.5° C.

| Elemental analysis for $C_{10}H_7O_3Br$: | | | |
|---|---|---|---|
| | C | H | Br |
| Calculated (%): | 47.09 | 2.77 | 31.33 |
| Found (%): | 47.35 | 2.69 | 31.15 |

IR (KBr, $\nu cm^{-1}$): near 1825 (carbonyl).

NMR (CCl$_4$, δppm): 4.35 (2H, —CH$_2$Br, s), 7.40 (5H, benzene proton, s).

EXAMPLE 6

Production of 4-bromomethyl-1,3-dioxolen-2-one 5.0 g of 4-methyl-1,3-dioxolen-2-one (synthesized in accordance with U.S. Pat. No. 3,020,290) was dissolved in 200 ml of benzene, and 4.7 g of sodium hydrogen carbonate and 40 mg of α,α'-azobisisobutyronitrile were added. Under a nitrogen gas atmosphere, 8.8 g of bromine in 40 ml of benzene was added dropwise over the course of 90 minutes with vigorous stirring at 60° C. Subsequently, the mixture was stirred for 30 minutes at the same temperature. After cooling, the insoluble materials were separated by filtration, and the filtrate was concentrated. There was obtained 9.0 g of a syrup. The syrup was subjected to NMR measurement and it was confirmed that the product was formed in a formation ratio of about 85%. The syrup was distilled under reduced pressure to give the desired product as a colorless liquid having a boiling point of 92° to 96° C./3 mmHg.

| Elemental analysis for $C_4H_3O_3Br$: | | | |
|---|---|---|---|
| | C | H | Br |
| Calculated (%): | 26.84 | 1.69 | 44.65 |
| Found (%): | 26.72 | 1.53 | 44.30 |

IR (neat, $\nu cm^{-1}$): near 1830 (carbonyl).

NMR (CCl$_4$, δppm): 4.10 (2H, —CH$_2$Br, s), 7.00

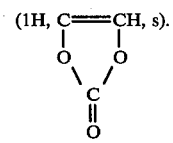

(1H, C=CH, s).

EXAMPLE 7

Production of 3-bromo-1,2-carbonyldioxycyclohexene 7.0 g of 1,2-carbonyldioxycyclohexene (synthesized in accordance with Tetrahedron Letters, 1972, pages 1701–1704) was dissolved in 200 ml of benzene, and 4.7 g of sodium hydrogen carbonate and 40 mg of α,α'-azobisisobutyronitrile were added. Under a nitrogen gas atmosphere, 8.8 g of bromine in 40 ml of benzene was added dropwise over the course of 70 minutes with vigorous stirring at 60° C. Subsequently, the mixture was stirred for 30 minutes at the same temperature. After cooling, the insoluble materials were separated by filtration, and the filtrate was concentrated at a low temperature under reduced pressure to give 11.0 g of the desired product as pale brown liquid (crude form). NMR data showed that the formation ratio of the product was about 85%.

IR (neat, $\nu cm^{-1}$): near 1825 (carbonyl).

NMR (CDCl$_3$, δppm): 1.3–3.0 (about 6H, cyclic methylene proton, m), 5.0

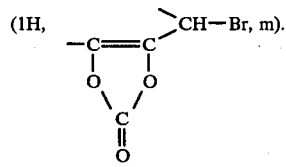

(1H, CH—Br, m).

REFERENTIAL EXAMPLE 1

Production of ampicillin (2,3-carbonyldioxy-2-cyclohexenyl) ester hydrochloride 500 mg of ampicillin trihydrate was dispersed in 6 ml of dimethylformamide, and 125 mg of potassium hydrogen carbonate was added. The mixture was cooled to 0° C., and 0.25 ml of benzaldehyde was further added. The mixture was stirred at 0° C. for 2.5 hours. Then, 125 mg of potassium hydrogen carbonate and 250 mg of 3-bromomethyl-1,2-carbonyldioxycyclohexane (the crude product obtained in Example 7) were added, and the mixture was further stirred for 3 hours at 0° C. After the reaction, the reaction mixture was poured into ice water and the precipitated solid was extracted with 30 ml of ethyl acetate. The organic layer was washed with three 20 ml portions of water, and dried over anhydrous magnesium sulfate. Ethyl acetate was evaporated under reduced pressure to form a yellow syrup.

The resulting syrupy residue was dissolved in 4 ml of acetonitrile, and adjusted to pH 2.0 with dilute hydrochloric acid. The solution was stirred at 0° C. for 30 minutes. Then, 10 ml of water was added, and acetonitrile was evaporated under reduced pressure. The aqueous layer was repeatedly washed with ethyl acetate and saturated with sodium chloride. The precipitated oily substance was extracted with 50 ml of methylene chloride, and washed with a saturated aqueous solution of sodium chloride. The methylene chloride solution was dried over anhydrous sodium sulfate, and then concentrated to half of its original amount. Then, 30 ml of isopropanol was added, and the mixture was again concentrated under reduced pressure to give a pale yellow solid.

The solid was collected by filtration and washed with isopropanol and ether to give 300 mg of ampicillin (2,3-carbonyldioxy-2-cyclohexenyl) ester hydrochloride as a colorless amorphous solid.

Melting point: 140° C. (decomp.).

IR (neat, $\nu cm^{-1}$): 1830 (cyclic carbonate), 1780 ($\beta$-lactam), 1750 (ester), 1690 (amide).

The resulting ampicillin ester hydrochloride was incubated at 37° C. for 10 minutes in 40% mouse blood, and then bioautographed. It was found that this compound changed completely to ampicillin.

REFERENTIAL EXAMPLE 2

Production of ampicillin (5-phenyl-2-oxo-1,3-dioxolen-4-yl)methyl ester hydrochloride In the same way as in Referential Example 1, ampicillin (5-phenyl-2-oxo-1,3-dioxolen-4-yl)methyl ester hydrochloride was obtained from ampicillin trihydrate and 4-bromomethyl-5-phenyl-1,3-dioxolen-2-one.

Yield: 50.5%.

Colorless amorphous solid.

Melting point: 140° C. (decomp.)

IR (KBr, $\nu cm^{-1}$): 1830 (cyclic carbonate), 1785 ($\beta$-lactam), 1760 (ester), 1690 (amide).

The resulting ampicillin (5-phenyl-2-oxo-1,3-dioxolen-4-yl)methyl ester hydrochloride was incubated at 37° C. for 5 minutes in 40% mouse blood, and then bioautographed. It was found that this compound completely changed to ampicillin.

REFERENTIAL EXAMPLE 3

Production of ampicillin (5-methyl-2-oxo-1,3-dioxolen-4-yl)methyl ester hydrochloride In the same way as in Referential Example 1, ampicillin (5-methyl-2-oxo-1,3-dioxolen-4-yl)methyl ester hydrochloride was obtained from ampicillin trihydrate and 4-bromomethyl-5-methyl-1,3-dioxolen-2-one.

Yield: 61.0%.

Colorless amorphous solid.

Melting point: Coloration began at 141° C., and foaming occurred at 145° C.

IR (KBr, $\nu cm^{-1}$): 1825 (cyclic carbonate), 1785 ($\beta$-lactam), 1750 (ester), 1690 (amide).

The product was incubated and bioautographed in the same way as in Referential Example 1. It was found that this product completely changed to ampicillin.

What is claimed is:

1. A process for producing a brominated 1,3-dioxolen-2-one of the following general formula (I)

$$\begin{array}{c} Br-CH-C=\!\!=\!\!C-R_1 \\ | \quad\quad | \quad\quad | \\ R_2 \quad O \quad\;\; O \\ \diagdown \;\; \diagup \\ C \\ \| \\ O \end{array} \quad (I)$$

wherein $R_1$ represents a hydrogen atom, a methyl group, or an aryl group, and $R_2$ represents a hydrogen atom, or $R_1$ and $R_2$ may be bonded together to form $-(CH_2)_n-$ in which n represents an integer of 3 to 5, which comprises reacting a compound of the following formula (II)

$$\begin{array}{c} CH_2-C=\!\!=\!\!C-R_1 \\ | \quad\quad | \quad\quad | \\ R_2 \quad O \quad\;\; O \\ \diagdown \;\; \diagup \\ C \\ \| \\ O \end{array} \quad (II)$$

wherein $R_1$ and $R_2$ are as defined, with bromine under radical generating conditions.

2. The process of claim 1 wherein the reaction is carried out in an aprotic inert organic solvent.

3. The process of claim 2 wherein the aprotic inert organic solvent is a halogenated aliphatic saturated hydrocarbon.

4. The process of claim 2 wherein the aprotic inert organic solvent is benzene or chlorobenzene.

5. The process of any one of claims 1 to 4 wherein the radical generating conditions are provided by ultraviolet irradiation.

6. The process of any one of claims 1 to 4 wherein the radical generating conditions are provided by the use of $\alpha,\alpha'$-azobisisobutyronitrile, $\alpha,\alpha'$-azobis-2,4-dimethylvaleronitrile, or benzoyl peroxide.

7. The process of any one of claims 1 to 4 wherein the amount of bromine is about 1.0 to about 1.5 moles for each 1.0 mole of the compound of general formula (II).

8. A process for producing a brominated 1,3-dioxolen-2-one of the following formula (I)

$$\begin{array}{c} Br-CH-C=\!\!=\!\!C-R_1 \\ | \quad\quad | \quad\quad | \\ R_2 \quad O \quad\;\; O \\ \diagdown \;\; \diagup \\ C \\ \| \\ O \end{array} \quad (I)$$

wherein R₁ represents a hydrogen atom, a methyl group, or an aryl group, and R₂ represents a hydrogen atom, or R₁ and R₂ may be bonded together to form —(CH₂)ₙ— in which n is an integer of 3 to 5, which comprises reacting a compound of the following formula (II)

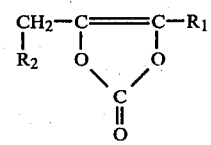

wherein R₁ and R₂ are as defined, with bromine in the presence of a basic inorganic compound under radical generating conditions.

9. The process of claim 8 wherein the basic inorganic compound is an alkali hydrogen carbonate or an alkali carbonate.

* * * * *

UNITED STATES PATENT AND TRADEMARK OFFICE
CERTIFICATE OF CORRECTION

PATENT NO. : 4,428,806

DATED : January 31, 1984

INVENTOR(S) : FUMIO SAKAMOTO, SHOJI IKEDA, GORO TSUKAMOTO and ISAMU UTSUMI

It is certified that error appears in the above—identified patent and that said Letters Patent are hereby corrected as shown below:

Column 1, line 65, change "trace" to --tract--.

Column 6, line 46, change the "IR" data to read:
  --IR (neat, $\nu cm^{-1}$): near 1825 (carbonyl).--

Column 9, line 11, correct the spelling of --carbonyldioxycyclohexene--.

Signed and Sealed this

Second Day of April 1985

[SEAL]

Attest:

DONALD J. QUIGG

Attesting Officer        Acting Commissioner of Patents and Trademarks